United States Patent

Goldmann et al.

[11] Patent Number: 5,750,783
[45] Date of Patent: May 12, 1998

US005750783A

[54] BENZYLOXY-SUBSTITUTED PHENYLGLYCINOLAMIDES

[75] Inventors: Siegfried Goldmann; Ulrich Müller, both of Wuppertal, Germany; Richard Connell, Trumbull, Conn.; Hilmar Bischoff; Dirk Denzer, both of Wuppertal, Germany; Rudi Grützmann, Solingen, Germany; Martin Beuck, Erkrath, Germany

[73] Assignee: Bayer Aktiengesellschaft, Leverkusen, Germany

[21] Appl. No.: 833,824

[22] Filed: Apr. 10, 1997

[30] Foreign Application Priority Data

Apr. 18, 1996 [DE] Germany ............... 196 15 263.1

[51] Int. Cl.⁶ ............... C07C 233/16; C07C 233/25; A61K 31/24; A61K 31/16
[52] U.S. Cl. ............... 564/166; 564/174; 514/617; 514/619; 514/622
[58] Field of Search ............... 514/617, 619, 514/622; 564/166, 174

[56] References Cited

U.S. PATENT DOCUMENTS 5,246,965  9/1993  Mainalan .................. 514/532
5,442,060  8/1995  Jikittara et al. .......... 544/106

FOREIGN PATENT DOCUMENTS 0033611  8/1981  European Pat. Off. .

*Primary Examiner*—Johann Richter
*Assistant Examiner*—Ebenezer Sackey
*Attorney, Agent, or Firm*—Sprung Kramer Schaefer & Briscoe

[57] ABSTRACT

Benzyloxy-substituted phenylglycinolamides are prepared by reaction of benzyloxy-substituted phenylacetic acids with phenylglycinols. The benzyloxy-substituted phenylglycinolamides are suitable as active compounds in medicaments, in particular in medicaments for the treatment of atherosclerosis.

10 Claims, No Drawings

BENZYLOXY-SUBSTITUTED PHENYLGLYCINOLAMIDES

The present invention relates to benzyloy- substituted phenylglycinolamides, processes for their preparation and their use as medicaments, in particular as antiatherosclerotic medicaments.

It is known that raised blood levels of triglycerides (hypertriglyceridaemia) and cholesterol (hypercholesterolaemia) are associated with the genesis of atherosclerotic vascular wall changes and coronary heart diseases.

A distinctly increased risk of the development of coronary heart diseases moreover exists if these two risk factors occur in combination, which in turn is accompanied by an overproduction of apolipoprotein B-100. There is therefore still a great need to make available effective medicaments for the control of atherosclerosis and coronary heart diseases.

The present inventions relates to benzyloxy-substituted phenylglycinolamides of the general formula (I)

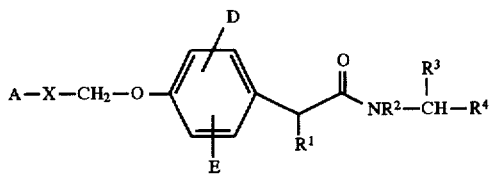

in which
A represents a 4- to 8-membered, saturated or partially unsaturated carbocycle, or represents phenyl, or represents a 5- to 6-membered aromatic heterocycle having up to 3 heteroatoms from the series S, N and/or O,
the abovementioned ring systems optionally being substituted up to 5 times identically or differently by phenyl, pyridyl, carboxyl, cyano, carboxyl, halogen, nitro, hydroxyl, by straight-chain or branched alkyl, alkoxy, alkoxycarbonyl, polyfluoroalkyl or polyfluoroalkoxy each having, up to 6 carbon atoms or by a group of the formula —$SO_2R^5$, —$NR^6R^7$ or —CO—$NR^8R^9$,
in which
$R^5$ denotes phenyl or straight-chain or branched alkyl having up to 3 carbon atoms,
$R^6$, $R^7$, $R^8$ and $R^9$ are identical or different and denote hydrogen or straight-chain or branched alkyl having up to 10 carbon atoms,
or
$R^8$ and $R^9$ denote cycloalkyl having 3 to 6 carbon atoms, or denote benzyl or phenyl, each of which is optionally substituted by halogen, nitro, hydroxyl or by straight-chain or branched alkyl or alkoxy each having up to 4 carbon atoms,
or
$R^8$ and $R^9$, together with the nitrogen atom, form a 5- to 7-membered, saturated or unsaturated heterocycle which can optionally contain a further heteroatom from the series S, N and/or O,
X represents a bond or the >C=O group,
D and B are identical or different and represent hydrogen, cycloalkyl having 3 to 8 carbon atoms, azido, hydroxyl, halogen, straight-chain or branched alkyl, alkoxy or alkenyl each having up to 6 carbon atoms,
$R^1$ represents cycloalkyl having 3 to 8 carbon atoms, or represents straight-chain or branched alkyl having up to 10 carbon atoms,
$R^2$ represents hydrogen or represents straight-chain or branched alkyl having up to 4 carbon atoms,
$R^3$ represents hydrogen or the —$CH_2$—OH group,
$R^4$ represents phenyl which is optionally substituted up to 3 times identically or differently by hydroxyl, halogen or straight-chain or branched alkyl having up to 5 carbon atoms,
and their salts.

The benzyloxy-substituted phenylglycinolamides according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulfonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as image and mirror image (enantiomers), or which do not behave as image and mirror image (diastereomers). The invention relates both to the enantiomers and to the diastereomers or their respective mixtures. These mixtures of the enantiomers and diastereomers can be separated in a known manner into the stereoisomerically uniform constituents.

A 4- to 8-membered, saturated or partially unsaturated carbocycle (A) in the context of the invention represents a cyclobutene, cyclopentene, cyclohexene, cycloheptene, cyclooctene, cyclopropyl, cyclobutyl, cyclopentyl, cyclohexyl or cycloheptyl radical. The cyclopentene, cyclohexene, cycloheptene, cyclopentyl, cyclohexyl and cycloheptyl radicals are preferred.

A 5- to 6-membered aromatic heterocycle (A) in the context of the invention in general represents, for example, thienyl, furyl, pyrimidyl or pyridyl. Pyridyl and thienyl are preferred.

Preferred compounds of the general formula (I) are those in which
A represents cyclopentyl, cyclohexyl, cyclopentenyl, cyclohexenyl, or represents pyridyl, phenyl or furyl, the abovementioned rings optionally being substituted up to 5 times identically or differently by phenyl, pyridyl, fluorine, chlorine, bromine, cyano, nitro, hydroxyl, carboxyl, by straight-chain or branched alkyl, alkoxy, alkoxycarbonyl, polyfluoroalkyl or polyfluoroalkoxy each having up to 3 carbon atoms or by a group of the formula —$SO_2R^5$, —$NR^6R^7$ or
—CO—$NR^8R^9$,
in which
$R^5$ denotes phenyl, methyl or ethyl,
$R^6$, $R^7$, $R^8$ and $R^9$ are identical or different and denote hydrogen or straight-chain or branched alkyl having up to 8 carbon atoms, or
- R⁸ and/or R⁹ denote cyclopropyl, cyclopentyl or cyclohexyl, or denote benzyl or phenyl, each of which is optionally substituted by fluorine, chlorine, bromine, nitro, hydroxyl or by straight-chain or branched alkyl or alkoxy each having up to 3 carbon atoms,
- or R⁸ and R⁹, together with the nitrogen atom, form a morpholinyl, pyrrolidinyl, pyridyl or piperidinyl ring, X represents a bond or the >C=O group, D and E are identical or different and represent hydrogen, cyclopropyl, cyclopentyl, cyclohexyl, azido, hydroxyl, fluorine, chlorine, bromine, straight-chain or branched alkyl, alkoxy or alkenyl each having up to 3 carbon atoms, R¹ represents cyclopropyl, cyclobutyl, cyclopentyl, cyclohexyl or cycloheptyl, or represents straight-chain or branched alkyl having up to 8 carbon atoms, R² represents hydrogen, or straight-chain or branched alkyl having up to 3 carbon atoms, R³ represents hydrogen or the —CH₂—OH group, R⁴ represents phenyl which is optionally substituted up to 2 times identically or differently by hydroxyl, fluorine, chlorine, bromine or straight-chain or branched alkyl having up to 4 carbon atoms, and their salts.

Particularly preferred compounds of the general formula (I) are those
in which

A represents cyclopentyl, cyclohexyl, cyclopentenyl, cyclohexenyl, or represents phenyl or pyridyl, the abovementioned rings optionally being substituted up to 3 times identically or differently by fluorine, chlorine, bromine, cyano, nitro, hydroxyl, by straight-chain or branched alkyl, alkoxy, alkoxycarbonyl each having up to 3 carbon atoms, trifluoromethyl, trifluoromethoxy, carboxyl, or by a group of the formula —SO₂R⁵, —NR⁶R⁷ or —CO—NR⁸R⁹,
in which
R⁵ denotes phenyl or methyl,
R⁶, R⁷, R⁸ and R⁹ are identical or different and denote hydrogen or straight-chain or branched alkyl having up to 6 carbon atoms,
or
R⁸ and/or R⁹ denote cyclopropyl, cyclopentyl or cyclohexyl, or denote benzyl or phenyl, each of which is optionally substituted by fluorine, chlorine, bromine, nitro, hydroxyl, methyl or methoxy,
or
R⁸ and R⁹, together with the nitrogen atom, form a morpholinyl, pyrrolidinyl or piperidinyl ring, X represents a bond or the >C=O group, D and E are identical or different and represent hydrogen, fluorine, chlorine or bromine, R¹ represents cyclopropyl, cyclobutyl, cyclopentyl, cyclohexyl or cycloheptyl, or represents straight-chain or branched alkyl having up to 8 carbon atoms, R² represents hydrogen, R³ represents hydrogen or the —CH₂—OH group, R⁴ represents phenyl which is optionally substituted up to 2 times identically or differently by hydroxyl, fluorine, chlorine, bromine or straight-chain or branched alkyl having up to 3 carbon atoms, and their salts.

Very particularly preferred compounds of the general formula (I) are those
in which D and E represent hydrogen
and R¹ represents cyclopentyl, cyclohexyl or cycloheptyl.

A process for the preparation of the compounds of the general formula (I) according to the invention has additionally been found, characterized in that carboxylic acids of the general formula (II)

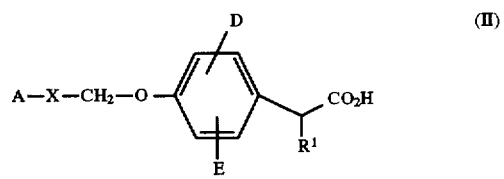

in which
A, D, B, X and R¹ have the meaning indicated, are reacted, if appropriate with prior activation of the carboxylic acid function, with compounds of the general formula (III)

in which
R², R³ and R⁴ have the meaning indicated, if appropriate under a protective gas atmosphere, if appropriate in inert solvents, in the presence of a base and/or auxiliary.

The process according to the invention can be illustrated by way of example by the following equation:

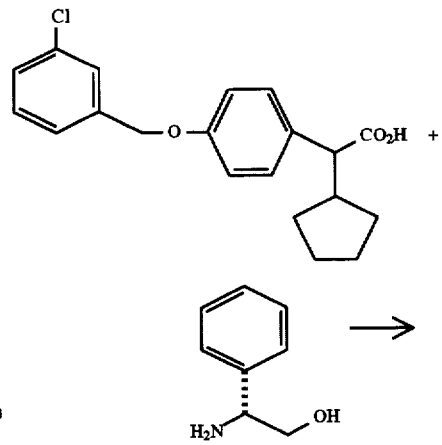

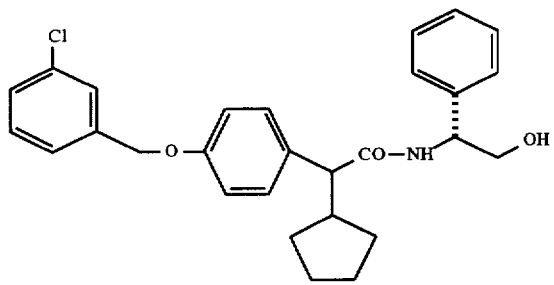

Suitable solvents here are inert organic solvents which do not change under the reaction conditions. These include ethers, such as diethyl ether or tetrahydrofuran, halogenohydrocarbons such as dichloromethane, trichloromethane, tetrachloromethane, 1,2-dichloroethane, trichloroethane, tetrachloroethane, 1,2-dichloroethyl or tricloroethylene, hydocarbons such as benzene, xylene, toluene, hexane, cyclohexane or petroleum fractions, nitromethane, dimethylformamide, acetone, acetonitrile or hexamethylphosphoramide. It is also possible to employ mixtures of the solvents. Dichloromethane, tetrahydrofuran, acetone and dimethylformamide are particularly preferred.

Suitable bases are the customary inorganic or organic bases. These preferably include alkali metal hydroxides such as, for example, sodium or potassium hydroxide, or alkali metal carbonates such as sodium or potassium carbonate, or alkali metal alkoxides such as, for example, sodium or potassium ethoxide, or sodium or potassium methoxide, or organic amines such as triethylamine, picoline or N-methylpiperidine, or amides such as sodium amide or lithium diisopropylamide, or organometallic compounds such as butyllithium or phenyllithium. Sodium and potassium carbonate and triethylamine are preferred.

The base is employed in an amount from 0.6 mol to 5 mol, preferably from 0.7 mol to 2 mol, relative to 1 mol of the compound of the general formula (II).

The reaction is in general carried out in a temperature range from 0° C. to 150° C., preferably from +20° C. to +110° C.

The reaction can be carried out at normal, elevated or at reduced pressure (e.g. 0.5 to 5 bar). In general, it is carried out at normal pressure.

For activation of the carboxylic acid function, in general bases and/or dehydrating reagents such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride, or isobutyl chloroformate or benzotriazolyloxy-tris-(dimethylamino)phosphonium hexafluorophosphate or diphenyl phosphoramidate or methanesulphonyl chloride are suitable, if appropriate in the presence of bases such as triethylamine or N-ethylmorpholine or N-methylpiperidine, or dicyclohexylcarbodiimide and N-hydroxysuccinimide.

The acid-binding agents and dehydrating reagents are in general employed in an amount from 0.5 to 3 mol, preferably from 1 to 1.5 mol, relative to 1 mol of the corresponding carboxylic acids.

The compounds of the general formula (II) are known in some cases or are new and can then be prepared, for example, by reacting compounds of the general formula (IV)

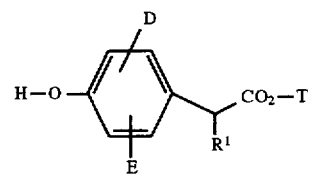

in which
and
D, B and $R^1$ have the meaning indicated,
T represents a typical hydroxyl protective group, preferably benzyl or tertbutyl,
after removal of this protective group according to customary methods,
with compounds of the general formula (V)

$$A-X-CH_2Y \qquad (V)$$

in which
A and X have the meaning indicated above
and
Y represents halogen, preferably bromine,
in inert solvents, if appropriate in the presence of a base, and, in the case of the acids, hydrolysing the esters.

The compounds of the general formulae (IV) and (V) are known per se or can be prepared by customary methods.

The compounds of the general formula (III) are likewise known or can be prepared by customary methods.

The compounds of the general formula (I) according to the invention have an unforeseeable spectrum of pharmacological action.

They can be used as active compounds in medicaments for the reduction of changes to vascular walls and for the treatment of coronary heart diseases, cardiac insufficiency, brain function disorders, ischaemic cerebral disorders, apoplexy, circulatory disorders, disorders of the microcirculation and thromboses.

The proliferation of smooth muscle cells furthermore plays a decisive part in the occlusion of vessels. The compounds according to the invention are suitable for inhibiting this proliferation and thus preventing atherosclerotic processes.

The compounds according to the invention are distinguished by a lowering of the ApoB-100-associated lipoproteins (VLDL and its degradation products, such as, for example, LDL), of ApoB-100, of triglycerides and of cholesterol. They thus have useful pharmacological properties, which are superior compared with the prior art.

Surprisingly, the action of the compounds according to the invention consists first in a decrease in or complete inhibition of the formation and/or the release of ApoB-100-associated lipoproteins from liver cells, which results in a lowering of the VLDL plasma level. This lowering of VLDL has to be accompanied by a lowering of the plasma levels of ApoB-100, LDL, triglycerides and of cholesterol; thus simultaneously several of the abovementioned risk factors which are involved in vascular wall changes are lowered.

The compounds according to the invention can therefore be employed for the prevention and treatment of atherosclerosis, obesity, pancreatitis and constipation.

1. Inhibition of the Release of ApoB-100-Associated Lipoproteins

The test for detecting the inhibition of the release of ApoB-100-associated lipoproteins from liver cells was carried out in vitro using cultured liver cells, preferably using cells of the human line HepG2. These cells are cultured under standard conditions in medium for the culture of eukaryotic cells, preferably in RPMI 1640 using 10% foetal calf serum. HepG2 cells synthesize and secrete into the culture supernatant ApoB-100-associated lipoprotein particles which in principle are built up in a similar manner to the VLDL and LDL particles which are to be found in the plasma.

These particles can be detected using an immunoassay for human LDL. This immunoassay is carried out using antibodies which have been induced under standard-conditions against human LDL in rabbits The anti-LDL antibodies (rabbit anti-LDL ABs) were purified by affinity chromatography on an immunosorbent using human LDL. These purified rabbit anti-LDL ABs are adsorbed on the surface of plastic. Expediently, this adsorption is carried out on the plastic surface of microtitre plates having 96 wells, preferably on MaxiSorp plates. If ApoB-100-associated particles are present in the supernatant of HepG2 cells, then these can bind to the insolubilized rabbit anti-LDL ABs, and an immune complex results which is bound to the plastic surface. Non-bound proteins are removed by washing. The immune complex situated on the plastic surface is detected using monoclonal antibodies which have been induced against human LDL and purified under standard conditions. These antibodies were conjugated with the enzyme peroxidase. Peroxidase converts the colourless substrate TMB into a coloured product in the presence of $H_2O_2$. After acidification of the reaction mixture with $H_2SO_4$, the specific light adsorption at 450 nm is determined, which is a measure of the amount of ApoB-100-associated particles which has been secreted into the culture supernatant by the HepG2 cells.

Surprisingly, the compounds according to the invention inhibit the release of ApoB-100-associated particles. The $IC_{50}$ indicates at which substance concentration the light adsorption is inhibited by 50% in comparison to the control (solvent control without substance).

2. Determination of VUDL Secretion in Vivo in the Hamster

The effect of the test substances on VLDL secretion in vivo is investigated in the hamster. To do this, golden hamsters are anaesthetized with Ketavet (83 mg/kg s.c.) and Nembutal (50 mg/kg. i.p.) after premedication with atropine (83 mg/kg s.c.). When the animals have become reflex-free, the jugular vein is exposed and cannulated. 0.25 ml/kg of a 20% strength solution of Triton WR-1339 in physiological saline solution is then administered. This detergent inhibits the lipoprotein lipase and thus leads to a rise in the triglyceride level on account of an absent catabolism of secreted VDDL particles. This triglyceride rise can be used as a measure of the VLDL secretion rate. Blood is taken from the animals by puncture of the retro orbital venous plexus before and one and two hours after administration of the detergent. The blood is incubated for two hours at room temperature, then overnight at 4° C. in order to end clotting completely. It is then centrifuged at 10.000 g for 5 minutes. In the serum thus obtained, the triglyceride concentration is determined with the aid of a modified commercially available enzyme test (Merckotest® triglycerides No. 14354). 100 µl of serum are treated with 100 µl of test reagent in 96-hole plates and incubated at room temperature for 10 minutes. The optical density is then determined at a wavelength of 492 nm in an automatic plate-reading apparatus (SLT spectra). Serum samples having too high a triglyceride concentration are diluted with physiological saline solution. The triglyceride concentration contained in the samples is determined with the aid of a standard curve measured in parallel. In this model, test substances are administered either intravenously immediately before administration of the detergent or orally or subcutaneously before initiation of anaesthesia.

3. Inhibition of Intestinal Triglyceride Absorption in Vivo (Rats)

The substances which are to be investigated for their triglyceride absorption-inhibiting action in vivo are administered orally to male Wistar rats having a body weight of between 170 and 230 g. For this purpose, the animals are divided into groups of 6 animals 18 hours before administration of substance and the feed is then withdrawn from them. Drinking water is available to the animals ad libitum. The animals of the control groups receive an aqueous tragacanth suspension or a tragacanth suspension which contains olive oil. The tragacanth-olive oil suspension is prepared using the Ultra-Turrax. The substances to be investigated are suspended in a corresponding tragacanth-olive oil suspension, likewise using the Ultra-Turrax, directly before substance administration.

Blood is taken from each rat by puncture of the retroorbital venous plexus before stomach tube application to determine the basal serum triglyceride content. The tragacanth suspension, the tragacanth-olive oil suspensions without substance (control animals), or the substances suspended in a corresponding tragacanth-olive oil suspension are then administered to the fasting animals using a stomach tube. Further taking of blood to determine the postprandial serum triglyceride rise is generally carried out 1, 2 and 3 hours after stomach tube application.

The blood samples are centrifuged and, after recovering the serum, the triglycerides are determined photometrically using an EPOS analyzer 5060 (Eppendorf Geratebau, Netheler & Hinz GmbH, Hamburg). The determination of the triglycerides is carried out completely enzymatically using a commercially available UV test.

The postprandial serum triglyceride rise is determined by subtraction of the triglyceride preliminary value of each animal from its corresponding postprandial triglyceride concentrations (1,2 and 3 hours after administration).

The differences (in mmol/1) at each time (1, 2 and 3 hours) are averaged in the groups, and the average values of the serum triglyceride rise ($\Delta TG$) of the substance-treated animals are compared with the animals which received only the tragacanth-oil suspension.

The serum triglyceride course of the control animals which received only tragacanth is likewise calculated. The substance effect at each time (1, 2 or 3 hours) is determined as follows and indicated in $\Delta\%$ of the oil-loaded control.

$$\Delta\% \text{ triglyceride rise} = \frac{\Delta TG_{substance} - \Delta TG_{tragacanth\ control}}{\Delta TG_{oil\ loading} - \Delta TG_{tragacanth\ control}} \times 100$$

Effect of 10 mg of test substance/kg of body weight p.o. on the triglyceride rise ($\Delta\%$) 2 h after a triglyceride loading, in the serum of fasting rats. The serum triglyceride rise of fat-loaded control animals relative to the serum triglyceride level of tragacanth control animals corresponds to 100%. n=6 animals per group.

Statistical analysis is carried out using Student's t-test after prior checking of the variances for homogeneity.

Substances which at one time statistically significantly ($p<0.05$) decrease the postprandial serum triglyceride rise by at least 30%, compared with the untreated control group, are regarded as pharmacologically active.

4. Inhibition of VLDL Secretion in Vivo (Rat)

The action of the test substances on VLDL secretion is likewise investigated in the rat. To do this, Triton WR-1339 (2.5 mg/kg ), dissolved in physiological saline solution, is administered intravenously into the tail vein of rats of 500 mg/kg body weight. Triton WR-1339 inhibits lipoprotein lipase and thus leads by inhibition of VLDL catabolism to a rise in the triglyceride and cholesterol level. These rises can be used as a measure of the VLDL secretion rate.

Blood is taken from the animals by puncture of the retroorbital venous plexus before and one and two hours after administration of the detergent. The blood is incubated at room temperature for 1 h for clotting and the serum is recovered by centrifugation at 10,000 g for 20 s. The triglycerides are then determined photometrically at a wavelength of 540 nm by means of a commercially available coupled enzyme test (Sigma Diagnostics®, No. 339). Measurement is carried out with the aid of a likewise coupled enzyme test (Boehringer Mannheim®, No. 1442350) at a wavelength of 546 nm. Samples having triglyceride or cholesterol concentrations which exceed the measuring range of the methods are diluted with physiological saline solution. The determination of the respective serum concentrations is carried out with the aid of standard series measured in parallel. Test substances are administered orally, intravenously or subcutaneously immediately after Triton injection.

The invention additionally relates to the combination of benzyloxy-substituted phenylglycinolamides of the general formula (I) with a glucosidase and/or amylase inhibitor for the treatment of familial hyperlipidaemias, of obesity (adiposity) and of diabetes mellitus. Glucosidase and/or amylase inhibitors in the context of the invention are, for example, acarbose, adiposine, voglibose, miglitol, emiglitate, MDL-25637, camiglibose (MDL-73945), tendamistate, AI-3688, trestatin, pradimicin-Q and salbostatin.

The combination of acarbose, miglitol, emiglitate or voglibose With one of the abovementioned compounds of the general formula (I) according to the invention is preferred.

The new active compounds can be converted in a known manner into the customary formulations, such as tablets, coated tablets,. pills, granules, aerosols, syrups, emulsions, suspensions and solutions, using inert, non-toxic, pharmaceutically suitable excipients or solvents. In this connection, the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, it being possible, for example, if water is used as a diluent optionally to use organic solvents as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proved advantageous in the case of intravenous administration to administer amounts of approximately 0.001 to 1 mg/kg, preferably, approximately 0.01 to 0.5 mg/kg, of body weight to achieve effective results, and in the case of oral administration the dose is approximately 0.01 to 20 mg/kg, preferably 0.1to 10 mg/kg, of body weight.

In spite of this, it may, if appropriate, be necessary to depart from the amounts mentioned, namely depending on the body weight or on the type of administration route, on individual behaviour towards the medicament, the manner of its formulation and the time or interval at which administration takes place. Thus, in some cases it may be adequate to manage with less than the abovementioned minimum amount, while in other cases the upper limit mentioned has to be exceeded. In the case of the administration of larger amounts, it may be advisable to divide these into several individual doses over the course of the day.

STARTING COMPOUNDS

Example I tert-Butyl 2-[4-(3-chlorobenzyloxyphenyl)-2-cyclopentyl]-acetate

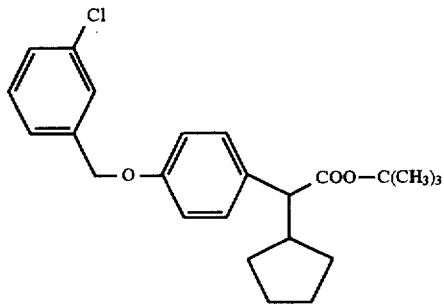

1 g of tert-butyl 2-(4-hydroxyphenyl)-2-cyclopentyl-acetate (U.S. Pat. No. 834,734) and 1.2 ml of 3-chlorobenzyl bromide are dissolved in 10 ml of DMF and heated at 60°–70° C. for 14 h with 0.9 g of $K_2CO_3$. After cooling, the mixture is treated with water and extracted by shaking with ether and the ether extract is dried. 1.3 g of the title compound are obtained as an oil. $R_f$=0.48 (cyclohexane / ethyl acetate 9:1)

Example II

2-[4-(3-Chlorobenzyloxyphenyl)-2-cyclopentyl]-acetic acid

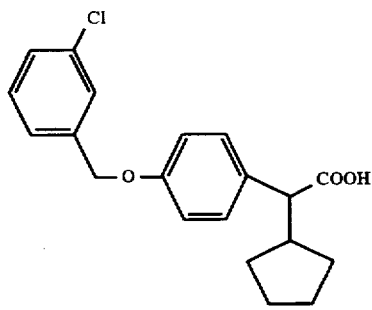

1.1 g of the compound from Example I are dissolved in 12 ml of dioxane and treated with 0.6 ml of conc. HCl, the mixture is heated at reflux for 8 h and concentrated, the residue is dissolved in $CH_2Cl_2$, and the solution is washed with water until neutral and concentrated. The residue is crystallized using $H_2O$. Yield: 0.6 g (60% of theory) M.P.: 99°–100° C.

Preparation Examples

Example 1

2-[4-(3-Chlorobenzyloxyphenyl)-2-cyclopentyl]-N-[(2-hydroxy)-1-(R)-phenylethyl]-2-acetamide

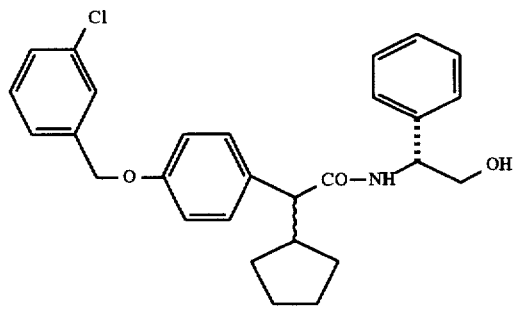

0.52 g of the compound from Example II is dissolved in 8 ml of THF, cooled to –30° C. and treated successively with 0.62 ml of triethylamine and 0.13 ml of mesylchloride and the mixture is stirred at –30° C. for 30 min. 0.25 g of (R)-(-)-2-hydroxy-1-phenyl-ethylamine and dimethylaminopyridine (both dissolved in 4 ml of THF) are then added dropwise at –30° C., and the mixture is stirred at –30° C. for 30 min and at room temperature for 2 h. 50% of the title compound is obtained. M.p. 148°–149° C.

The compounds listed in Table 1 are prepared in analogy to the procedure of Example 1:

TABLE 1

| Ex. No. | A | X | $R^1$ | $R^{10}$ | Mp. (°C.) | $R_f$* |
|---|---|---|---|---|---|---|
| 2 | 2-pyridyl | bond | cyclopentyl | 1-phenyl-2-hydroxyethyl | 145–7 | |
| 3 | phenyl | bond | cyclopentyl | 1-phenyl-2-hydroxyethyl | 179–80 | |
| 4 | cyclohexyl | bond | cyclopentyl | 1-phenyl-2-hydroxyethyl | 155–6 | |
| 5 | 3-chloro-5-methylphenyl | C(=O) | cyclopentyl | benzyl | amorphous | 0.5 [1] |

TABLE 1-continued

A—X—H₂C—O—⟨phenyl⟩—CH(R¹)—CO—NH—R¹⁰

| Ex. No. | A | X | R¹ | R¹⁰ | Mp. (°C.) | $R_f$* |
|---|---|---|---|---|---|---|
| 6 | 2,4,6-trimethylphenyl | C=O | cyclopentyl | -CH(CH₃)CH₂OH (phenyl) | amorphous | 0.25 and 0.31 ¹⁾ |
| 7 | 2,4,6-trimethylphenyl | C=O | cyclopentyl | -CH(CH₂CH₃)(phenyl) | amorphous | 0.34 ²⁾ |
| 8 | 2-fluorophenyl | bond | cyclopentyl | -CH(CH₃)CH₂OH (phenyl) | 167 | |
| 9 | 2-chlorophenyl | bond | cyclopentyl | -CH(CH₃)CH₂OH (phenyl) | 139–40 | |
| 10 | 2-chlorophenyl | bond | cycloheptyl | -CH(CH₃)CH₂OH (phenyl) | amorphous | 0.48 and 0.40 ¹⁾ |
| 11 | 3-chlorophenyl | bond | cycloheptyl | -CH(CH₃)CH₂OH (phenyl) | 155–7 | |
| 12 | 4-chlorophenyl | bond | cyclopentyl | -CH(CH₃)CH₂OH (phenyl) | 165–6 | |
| 13 | 4-chlorophenyl | bond | cycloheptyl | -CH(CH₃)CH₂OH (phenyl) | 175–6 | |

TABLE 1-continued

A—X—H₂C—O—[phenyl with R¹]—CO—NH—R¹⁰

| Ex. No. | A | X | R¹ | R¹⁰ | Mp. (°C.) | R_f* |
|---|---|---|---|---|---|---|
| 14 | 2-NO₂-phenyl | bond | cyclopentyl | (S)-1-phenyl-2-hydroxyprop-1-yl | 152–3 | |
| 15 | 2-NO₂-phenyl | bond | cycloheptyl | (S)-1-phenyl-2-hydroxyprop-1-yl | amorphous | 0.37 and 0.33 ¹⁾ |
| 16 | 3-NO₂-phenyl | bond | cyclopentyl | (S)-1-phenyl-2-hydroxyprop-1-yl | 144–5 | |
| 17 | 4-NO₂-phenyl | bond | cyclopentyl | (S)-1-phenyl-2-hydroxyprop-1-yl | 160–3 | |
| 18 | 4-NO₂-phenyl | bond | cycloheptyl | (S)-1-phenyl-2-hydroxyprop-1-yl | amorphous | |
| 19 | 2-CH₃-phenyl | bond | cyclopentyl | (S)-1-phenyl-2-hydroxyprop-1-yl | 144–6 | |
| 20 | 2-CH₃-phenyl | bond | cycloheptyl | (S)-1-phenyl-2-hydroxyprop-1-yl | 132–4 | |
| 21 | 3-CH₃-phenyl | bond | cyclopentyl | (S)-1-phenyl-2-hydroxyprop-1-yl | 151–3 | |

TABLE 1-continued

A—X—H₂C—O—C₆H₄—CR¹H—CO—NH—R¹⁰

| Ex. No. | A | X | R¹ | R¹⁰ | Mp. (°C.) | R_f* |
|---|---|---|---|---|---|---|
| 22 | 4-H₃C-C₆H₄- | bond | cyclopentyl | -CH(CH₃)CH₂OH (Ph) | 175–7 | |
| 23 | 2,3-(CH₃)₂-C₆H₃- | bond | cyclopentyl | -CH(CH₃)CH₂OH (Ph) | 144 | |
| 24 | 2-CF₃-C₆H₄- | bond | cyclopentyl | -CH(CH₃)CH₂OH (Ph) | 160–2 | |
| 25 | 2-CN-C₆H₄- | bond | cyclopentyl | -CH(CH₃)CH₂OH (Ph) | 158–9 | |
| 26 | 3-CH₃OOC-C₆H₄- | bond | cyclopentyl | -CH(CH₃)CH₂OH (Ph) | 156–7 | |
| 27 | 4-H₃CSO₂-C₆H₄- | bond | cyclopentyl | -CH(CH₃)CH₂OH (Ph) | amorphous | 0.10 [1)] |
| 28 | 4-F₃CO-C₆H₄- | bond | cyclopentyl | -CH(CH₃)CH₂OH (Ph) | 186–8 | |
| 29 | 2-pyridyl | bond | cycloheptyl | -CH(CH₃)CH₂OH (Ph) | | 0.19 [1)] |

TABLE 1-continued

A—X—H$_2$C—O—⟨phenyl⟩—CH(R$^1$)—CO—NH—R$^{10}$

| Ex. No. | A | X | R$^1$ | R$^{10}$ | Mp. (°C.) | R$_f$* |
|---|---|---|---|---|---|---|
| 30 | 2-COOH-phenyl | bond | cyclopentyl | (S)-CH(CH$_3$)CH$_2$OH phenyl | 182–3 | |
| 31 | 2-COOH-phenyl | bond | cyclopentyl | benzyl (CH$_2$-phenyl) | 177–8 | |
| 32 | 2-COOCH$_3$-phenyl | bond | cyclopentyl | (S)-CH(CH$_3$)CH$_2$OH phenyl | 152–3 | |
| 33 | 2-COOCH$_3$-phenyl | bond | cyclopentyl | benzyl | 115–6 | |
| 34 | 2-(CONHPh)-phenyl | bond | cyclopentyl | (S)-CH(CH$_3$)CH$_2$OH phenyl | amorphous | 0.67 [1)] |
| 35 | 2-(CONHPh)-phenyl | bond | cyclopentyl | benzyl | amorphous | 0.29 [2)] |
| 36 | 2-(CONHCH$_3$·phenyl)-phenyl | bond | cyclopentyl | (S)-CH(CH$_3$)CH$_2$OH phenyl | amorphous | 0.22 [1)] |
| 37 | 2-(CONHCH$_3$·phenyl)-phenyl | bond | cyclopentyl | benzyl | 165–6 | |

TABLE 1-continued

A—X—H₂C—O—[phenyl]—CO—NH—R¹⁰ with R¹ substituent

| Ex. No. | A | X | R¹ | R¹⁰ | Mp. (°C.) | R_f* |
|---|---|---|---|---|---|---|
| 38 | 2-(cyclohexyl-NH-CO)-phenyl | bond | cyclopentyl | phenyl-CH(CH₃)-CH₂OH | amorphous | 0.26 ¹⁾ |
| 39 | 2-(cyclohexyl-NH-CO)-phenyl | bond | cyclopentyl | benzyl | 157–8 | |
| 40 | 2-(piperidin-1-yl-CO)-phenyl | bond | cyclopentyl | phenyl-CH(CH₃)-CH₂OH | amorphous | 0.13 ¹⁾ |
| 41 | 2-(piperidin-1-yl-CO)-phenyl | bond | cyclopentyl | benzyl | amorphous | 0.08 ²⁾ 0.30 ¹⁾ |
| 42 | 2-(morpholin-4-yl-CO)-phenyl | bond | cyclopentyl | phenyl-CH(CH₃)-CH₂OH | amorphous | 0.04 ¹⁾ |
| 43 | 2-(morpholin-4-yl-CO)-phenyl | bond | cyclopentyl | | amorphous | |

¹⁾ Cyclohexane/EA = 1:1
²⁾ Cyclohexane/EA = 7:3

We claim:

1. Benzyloxy-substituted phenylglycinolamides of the general formula (I)

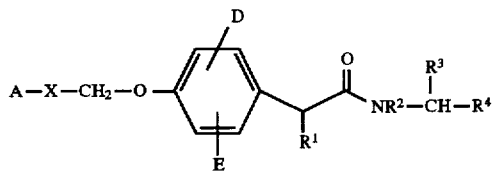

in which

A represents a 4- to 8-membered, saturated or partially unsaturated carbocycle, or represents phenyl, or represents a 5- to 6-membered aromatic heterocycle having up to 3 heteroatoms from the series S, N and/or O, the abovementioned ring systems optionally being substituted up to 5 times identically or differently by phenyl, pyridyl, carboxyl, cyano, carboxyl, halogen, nitro, hydroxyl, by straight-chain or branched alkyl, alkoxy, alkoxycarbonyl, polyfluoroalkyl or polyfluoroalkoxy each having up to 6 carbon atoms or by a group of the formula —SO₂R⁵, —NR⁶R⁷ or —CO—NR⁸R⁹, in which R⁵ denotes phenyl or straight-chain or branched alkyl having up to 3 carbon atoms, R⁶, R⁷, R⁸ and R⁹ are identical or different and denote hydrogen or straight-chain or branched alkyl having up to 10 carbon atoms, or R⁸ and R⁹ denote cycloalkyl having 3 to 6 carbon atoms, or denote benzyl or phenyl, each of which is optionally substituted by halogen, nitro, hydroxyl or by straight-chain or branched alkyl or alkoxy each having up to 4 carbon atoms, or R⁸ and R⁹, together with the nitrogen atom, form a 5- to 7-membered, saturated or unsaturated heterocycle which can optionally contain a further heteroatom from the series S, N and/or O, X represents a bond or the >C=O group, D and E are identical or different and represent hydrogen, cycloalkyl having 3 to 8 carbon atoms, azido, hydroxyl, halogen, straight-chain or branched alkyl, alkoxy or alkenyl each having up to 6 carbon atoms, R¹ represents cycloalkyl having 3 to 8 carbon atoms, or represents straight-chain or branched alkyl having up to 10 carbon atoms, R² represents hydrogen or represents straight-chain or branched alkyl having up to 4 carbon atoms, R³ represents hydrogen or the —CH₂—OH group, R⁴ represents phenyl which is optionally substituted up to 3 times identically or differently by hydroxyl, halogen or straight-chain or branched alkyl having up to 5 carbon atoms, and their salts.

2. Benzyloxy-substituted phenylglycinolamides of the formula according to claim 1 in which

A represents cyclopentyl, cyclohexyl, cyclopentenyl, cyclohexenyl, or represents pyridyl, phenyl or furyl, the abovementioned rings optionally being substituted up to 5 times identically or differently by phenyl, pyridyl, fluorine, chlorine, bromine, cyano, nitro, hydroxyl, carboxyl, by straight-chain or branched alkyl, alkoxy, alkoxycarbonyl, polyfluoroalkyl or polyfluoroalkoxy each having up to 3 carbon atoms or by a group of the formula —SO₂R⁵, —NR⁶R⁷ or —CO—NR⁸R⁹, in which R⁵ denotes phenyl, methyl or ethyl, R⁶, R⁷, R⁸ and R⁹ are identical or different and denote hydrogen or straight-chain or branched alkyl having up to 8 carbon atoms, or R⁸ and/or R⁹ denote cyclopropyl, cyclopentyl or cyclohexyl, or denote benzyl or phenyl, each of which is optionally substituted by fluorine, chlorine, bromine, nitro, hydroxyl or by straight-chain or branched alkyl or alkoxy each having up to 3 carbon atoms, or R⁸ and R⁹, together with the nitrogen atom, form a morpholinyl, pyrrolidinyl, pyridyl or piperidinyl ring, X represents a bond or the >C=O group, D and E are identical or different and represent hydrogen, cyclopropyl, cyclopentyl, cyclohexyl, azido, hydroxyl, fluorine, chlorine, bromine, straight-chain or branched alkyl, alkoxy or alkenyl each having up to 3 carbon atoms, R¹ represents cyclopropyl, cyclobutyl, cyclopentyl, cyclohexyl or cycloheptyl, or represents straight-chain or branched alkyl having up to 8 carbon atoms, R² represents hydrogen, or straight-chain or branched alkyl having up to 3 carbon atoms, R³ represents hydrogen or the —CH₂—OH group, R⁴ represents phenyl which is optionally substituted up to 2 times identically or differently by hydroxyl, fluorine, chlorine, bromine or straight-chain or branched alkyl having up to 4 carbon atoms, and their salts.

3. Benzyloxy-substituted phenylglycinolamides of the formula according to claim 1 in which

A represents cyclopentyl, cyclohexyl, cyclopentenyl, cyclohexenyl or represents phenyl or pyridyl, the abovementioned rings optionally being substituted up to 3 times identically or differently by fluorine, chlorine, bromine, cyano, nitro, hydroxyl, by straight-chain or branched alkyl, alkoxy, alkoxycarbonyl each having up to 3 carbon atoms, trifluoromethyl, trifluoromethoxy, carboxyl, or by a group of the formula —SO₂R⁵, —NR⁶R⁷ or —CO—NR⁸R⁹, in which R⁵ denotes phenyl or methyl, R⁶, R⁷, R⁸ and R⁹ are identical or different and denote hydrogen or straight-chain or branched alkyl having up to 6 carbon atoms, or R⁸ and R⁹ denote cyclopropyl, cyclopentyl or cyclohexyl, or denote benzyl or phenyl, each of which is optionally substituted by fluorine, chlorine, bromine, nitro, hydroxyl, methyl or methoxy, or R⁸ and R⁹, together with the nitrogen atom, form a morpholinyl, pyrrolidinyl or piperidinyl ring, X represents a bond or the >C=O group, D and B are identical or different and represent hydrogen, fluorine, chlorine or bromine, R¹ represents cyclopropyl, cyclobutyl, cyclopentyl, cyclohexyl or cycloheptyl, or represents straight-chain or branched alkyl having up to 8 carbon atoms, R² represents hydrogen, R³ represents hydrogen or the —CH₂—OH group,.

R⁴ represents phenyl which is optionally substituted up to 2 times identically or differently by hydroxyl, fluorine, chlorine, bromine or straight-chain or branched alkyl having up to 3 carbon atoms, and their salts.

4. Benzyloxy-substituted phenylglycinolamides of the formula according to claim 1 in which

D and E represent hydrogen and

R¹ represents cyclopentyl, cyclohexyl or cycloheptyl.

5. Benzyloxy-substituted phenylglycinolamides according to claim 1 wherein such compound is 2-[4-(3-chlorobenzyloxyphenyl)-2-cyclopentyl]-N-[(2-hydroxy)-1-(R)-phenylethyl]-acetamide of the formula

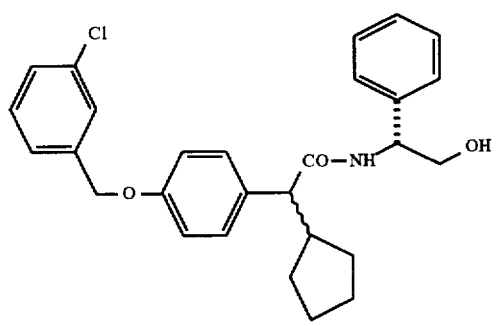

and salts thereof.

6. Benzyloxy-substituted phenylglycinolamides according to claim 1 wherein such compound is 2-[4-(2,4,6-trimethylbenzyl-methoxy) phenyl]-2-cyclopentyl-N-benzyl-acetamide of the formula

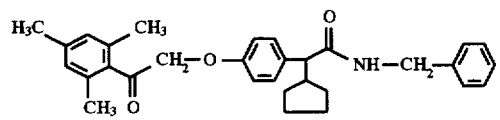

and salts thereof.

7. Benzyloxy-substituted phenylglycinolamides according to claim 1 wherein such compound is 2-[4-(4-nitrobenzyloxy)phenyl ]-2-cyclopentyl-N-[(2-hydroxy)-1-(R)-phenylethyl]-acetamide of the formula

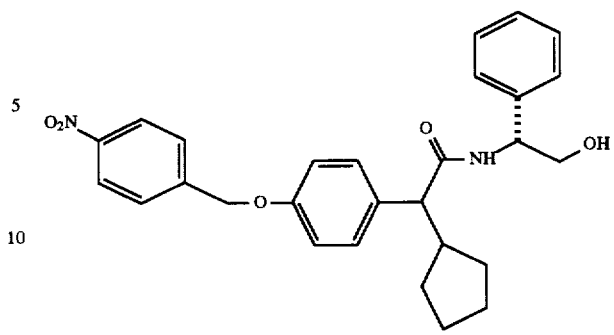

and salts thereof.

8. Benzyloxy-substituted phenylglycinolamides according to claim 1 wherein such compound is 2-[4-(2-methylbenzyloxy)phenyl ]-2-cycloheptyl-N-[(2-hydorxy)-1-(R)-phenylethyl]-acetamide of the formula

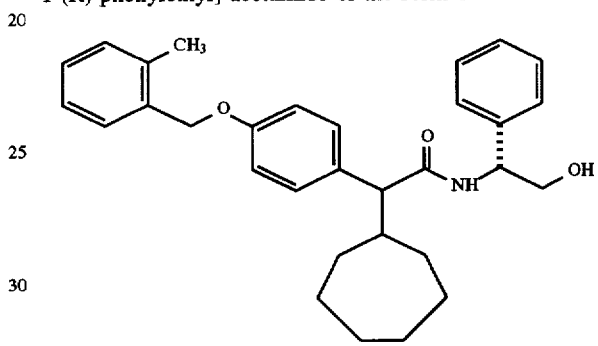

and salts thereof.

9. A composition for the treatment of atherosclerosis comprising an amount effective therefore of a compound or salt thereof according to claim 1 and a pharmacologically acceptable diluent.

10. The method of treating atherosclerosis in a patient in need thereof which comprises administering to such patient an amount effective therefore of a compound or salt thereof according to claim 1.

* * * * *

UNITED STATES PATENT AND TRADEMARK OFFICE
CERTIFICATE OF CORRECTION

PATENT NO. : 5,750,783
DATED : May 12, 1998
INVENTOR(S) : Siegfried Goldmann, et al.

It is certified that error appears in the above-identified patent and that said Letters Patent is hereby corrected as shown below:

On the title page, item [56] insert the following

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 9 | 7 | 0 | 2 | 1 | 5 | 11/13/90 | Mohrs, et al. | | | |
| | | 5 | 6 | 4 | 6 | 1 | 6 | 2 | 07/08/97 | Muller, et al. | | | |

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | AL | 3 | 4 | 4 | 5 | 1 | 9 | 12/6/89 | EP | | | | |
| | | AM | 7 | 1 | 6 | 0 | 8 | 2 | 06/12/96 | EP | | | | |

Signed and Sealed this

Ninth Day of February, 1999

Attest:

Attesting Officer

Acting Commissioner of Patents and Trademarks

UNITED STATES PATENT AND TRADEMARK OFFICE
CERTIFICATE OF CORRECTION

PATENT NO : 5,750,783
DATED : May 12, 1998
INVENTOR(S): Goldmann, et al.

It is certified that error appears in the above-identified patent and that said Letters Patent is hereby corrected as shown below:

Col. 24, Line 40          Delete "D and B" and substitute --D and E--

Signed and Sealed this

Twelfth Day of October, 1999

Q. TODD DICKINSON

Attest:

Attesting Officer          Acting Commissioner of Patents and Trademarks